United States Patent
Bevirt et al.

(10) Patent No.: US 6,325,114 B1
(45) Date of Patent: Dec. 4, 2001

(54) PIPETTING STATION APPARATUS

(75) Inventors: JoeBen Bevirt, Emerald Hills; Gabriel Noah Brinton, Palo Alto; Eric Rollins, Mt. View, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/495,106

(22) Filed: Feb. 1, 2000

(51) Int. Cl.$^7$ .......................... G01N 35/04; G01N 35/10
(52) U.S. Cl. ................. 141/130; 141/1; 422/65; 422/67; 422/100; 73/864.11; 73/864.17; 73/864.24; 73/864.25
(58) Field of Search .................. 141/1, 130; 422/65, 422/67, 100; 73/864.11, 864.16, 864.17, 864.24, 864.25

(56) References Cited

U.S. PATENT DOCUMENTS

| | | | |
|---|---|---|---|
| 4,077,444 | * 3/1978 | Gilson et al. | 141/130 |
| 4,478,094 | * 10/1984 | Salomaa et al. | 422/65 |
| 4,483,927 | * 11/1984 | Takekawa | 422/65 |
| 4,582,990 | 4/1986 | Stevens | 250/328 |
| 4,681,742 | 7/1987 | Johnson et al. | 422/102 |
| 5,102,623 | * 4/1992 | Yamamoto et al. | 422/65 |
| 5,122,342 | * 6/1992 | McCulloch et al. | 422/65 |
| 5,226,462 | 7/1993 | Carl | 141/1 |
| 5,245,530 | 9/1993 | Taki | 364/167.01 |
| 5,309,959 | * 5/1994 | Shaw et al. | 141/130 |
| 5,356,525 | 10/1994 | Goodale et al. | 204/299 |
| 5,443,791 | 8/1995 | Cathcart et al. | 422/65 |
| 5,598,270 | 1/1997 | Meisser et al. | 356/400 |
| 5,640,002 | 6/1997 | Rupper et al. | 235/472 |
| 5,661,287 | 8/1997 | Schaefer et al. | 253/383 |
| 5,811,306 | 9/1998 | Komatsu | 436/54 |
| 5,865,224 | * 2/1999 | Allly et al. | 141/130 |
| 5,988,236 | * 11/1999 | Fawcett | 141/130 |
| 6,063,579 | 5/2000 | Bevirt et al. | 435/6 |
| 6,148,878 | * 11/2000 | Ganz et al. | 141/130 |
| 6,160,905 | 12/2000 | Ahn et al. | 382/141 |

FOREIGN PATENT DOCUMENTS

| | | |
|---|---|---|
| 292995 | 11/1988 | (EP). |
| 301583 | 2/1989 | (EP). |
| 351988 | 1/1990 | (EP). |
| WO92/12233 | 7/1992 | (WO). |
| WO99/15905 | 4/1999 | (WO). |

OTHER PUBLICATIONS

CCS Packard, "Robotic Systems for Laboratory Automation", dated May 2, 2000.

Innovations Magazine, "M13 DNA Preparations for a Large Scale Sequencing Project Using the Hydra–96™ Channel Microdispenser", dated May 2, 2000.

Zymark Corporation, "RapidPlate 96/384 Pipetting Station", dated May 2, 2000.

Tomtec, "1536–Well Indexing Unit Quadra98® Accessory", dated May 2, 2000.

Beckman Coulter, "Biomek® 2000 Workstation", dated Jan. 12, 2000.

(List continued on next page.)

*Primary Examiner*—J. Casimer Jacyna
(74) *Attorney, Agent, or Firm*—Howrey Simon Arnold & White LLP

(57) ABSTRACT

A pipette station is described for use in the field of sample analysis. The pipette station increases the rate and ease with which a liquid may be manipulated into and out of sample carriers such as microwell plates. The pipette station includes shafts in the X, Y, and Z direction which possess ball screws which are integrated with motor shafts thus improving accuracy and eliminating the need for a coupling apparatus thereby reducing the space required for the pipette station. The pipette station may be interfaced with an automated laboratory system.

22 Claims, 11 Drawing Sheets

OTHER PUBLICATIONS

Beckman Coulter, "Liquid–Handling Tools", dated Jan. 12, 2000.

Beckman Coulter, "Multimek™ 96 Accurate, Intuitive 96–to 384–Well Automated Microplate Pipetting", dated Jan. 12, 2000.

Beckman Coulter, "Multimek™ 96 Product Specifications", dated Jan. 12, 2000.

PCT/US01/03298 Search Report Dated May 29, 2001.

NB8911116 IBM Technical Disclosure; November 1989.

NN950941 IBM Technical Disclosure; September 1995.

* cited by examiner

PIPETTING STATION APPARATUS

BACKGROUND OF THE INVENTION

1. Field of the Invention

The invention relates to the field of sample analysis. More particularly, this invention relates to an apparatus and method for increasing the rate at which microwell plates can be manipulated in performing various experiments. Namely, this invention relates to an apparatus and method of performing a pipetting operation on multiple microwell plates in a compact area.

2. Description of the Related Art

In the field of molecular biology, the process of sequencing nucleic acids has become significant as more and more diseases are linked to genetic abnormalities. The process of identifying genes and their corresponding proteins for potential therapeutic applications is well known.

Other types of molecular biology procedures are also important for therapeutic and research purposes including DNA restriction mapping, DNA probe generation, replication, DNA sample processing, and cycle sequencing. Generally, these procedures involve a substantial number of steps including, without limitation, automated liquid handling, robotic movement of the samples, pipetting of small amounts of many different reagents into a sample, and heating the samples within a given temperature range. These protocols includes a lengthy series of steps which must be performed in the correct order with absolute precision. Further, such assays are often done on multiple samples that require the manipulation of samples in sample carriers in a uniform fashion.

For instance, during clinical analysis of blood chemistry, various reagents and catalysts are mixed with blood samples in given amounts and in particular sequences. This analysis can yield the level of HDL cholesterol, LDL cholesterol, lipids, etc. present in the blood. By having multiple samples in a sample carrier, several samples may be analyzed at any give time. Similarly, in the area of new drug discovery, it is desirable to investigate numerous candidates for therapeutic agents. Given the great number of potential candidates, automated testing is desirable.

Because of the expense of the equipment required to perform these protocols accurately, increasing the throughput of the equipment performing these protocols becomes important for laboratories such as microbiology laboratories. It is desirable to increase the rate at which these protocols are performed while retaining, or even increasing, the quality of performance of the protocols. Automation is one method by which the rate of performing the protocols may be increased. By increasing the rate at which these protocols are performed, the protocols may be performed at a reduced cost.

Regardless of the type of experiment to be performed, sample carriers are generally employed so that more than one sample may be processed at any given time. For example, microwell, or microtitre, plates are generally utilized in these sample analysis protocols. Microwell plates are plastic plates containing uniformly-spaced cavities for holding various liquids. Generally, these commercially available microwell plates contain eight rows of twelve microwells for an industry-standard ninety-six microwell plate, or sixteen rows of twenty-four microwells for an industry-standard three hundred eighty-four microwell plate. Other sizes are also commercially available.

It is generally known to perform a protocol with automation as follows. Multiple microwell plates are stacked in one location. A transfer mechanism transfers one of the microwell plates onto a conveyor. Once the pipetting operation is complete, the conveyor transports the microwell plate to the desired station, e.g. a pipetting station. The conveyor then takes the microwell plate to the next station, and so on until the desired protocol has been performed on that microwell plate. Upon completion, that microwell plate is transferred by another transfer mechanism to a completion area for further processing.

In many experiments, it is important to maintain a constant, or even a germ-free, environment. Thus, it is often desired to enclose the samples and the automation equipment. Therefore, it is often desired to minimize the size of pipetting stations and the rest of the automated laboratory equipment, thus minimizing the size of the area that needs to be enclosed.

Because the pipetting operation is generally an important part of any standard protocol, much effort has been expended by the industry to increase the speed, accuracy, and quality of the pipetting operation, and reducing the size of the pipetting operation.

It is desirable to process a large number of samples in a single procedure. Further, pipetting requires dispensing small volumes of samples and other liquids into small containers which are small targets for the pipette. Thus accuracy and resolution are even more important for utilizing these small microwell cavity targets.

Therefore, it is desirable to have a pipetting station for performing liquid transfers of very small quantities of liquids in such a manner that avoids carryover and evaporation. This desired pipetting station should be modular for use in an automated laboratory. Further, it would be desirable for the pipetting station to be able to process a relatively large number of microwell plates, in a relatively small time. Further, it would be desirable for the pipetting operation to be performed accurately, in a relatively small space. And it would be desirable for the pipetting station to be able multitask such that the pipetting operation could be performed on one microwell tray, while other operations are being performed on other microwell trays. Finally, it is desired that a pipetting station have means to verify that the pipetting operation is being performed on the intended microwell plate, thus improving the quality and integrity of the pipetting operation.

Current pipetting stations, such as the MULTIMEK 96 and the BIOMEK 2000 Workstation, both from Beckman Coulter, Inc., are not capable of handling microwell plates that are stacked on vertically-spaced shelves. Therefore, microwell plates must be placed side by side on a table. However, as the number of microwells to be manipulated increases, the surface area required to spread out these microwell trays becomes prohibitive, especially if the work area is to be enclosed.

Similarly, U.S. Pat. No. 5,443,791 to Cathcart, et. al, discloses such a pipetting station, again with microwell plates that are stored side-by-side in a work area and having a relatively small footprint.

Therefore, there is a need for a pipetting station that can process a relatively large number of microwell plates in a comparatively small area.

Another problem with current pipetting systems is that no method exists for automatically ensuring that the pipette station is pipetting into the correct microwell tray. If a tray is mistakenly placed in the pipetting station, the pipetting station will perform the pipetting function without detecting the wrong microwell tray. Thus, it is desirable to have an automatic system to ensure that the correct microwell tray is being processed by the pipetting station thereby improving the quality control and integrity of the protocol.

Thus, despite years of effort, the method of transferring liquid into sample carriers such as microwell plates continues to be slower, less accurate, larger, and more expensive than would be desired.

The present invention is directed to overcoming, or at least reducing the effects of, one or more of the problems set forth above.

SUMMARY OF THE INVENTION

In accordance with some embodiments of the present invention, a pipetting station is described for transferring liquid from one container to another to perform a protocol, comprising a back plate having at least one horizontal slot and at least one vertical slot, at least one substantially horizontally movable shelf, said shelf being movably attached to said back plate in a cantilever fashion, said shelf being functionally associated with said horizontal slot, said shelf adapted to receive a container to hold said liquid, a shelf driving means functionally associated with said shelf to move said shelf in a horizontal direction along said horizontal slot, an X-Y head being movably attached to said at least one vertical slot in said back plate, a modular pipette head attached to said X-Y head functionally adapted to aspirate and dispense liquid into and out of said container, a Z-axis driving means functionally associated with said back plate and said X-Y head to move said X-Y head in a vertical direction, and a control system being functionally associated with said shelf driving means to selectively engage said shelf driving means, the control system selectively engaging said Z-axis driving means to move said X-Y head in a vertical direction, wherein said control system controls said shelf and said X-Y head to cooperatively move to perform said protocol. In some embodiments, the Z-axis driving means has an integrated Z-drive ball screw and motor shaft.

In some embodiments, a cylinder piston is described that includes at least one O-ring and at least one end-of-travel spring to dampen the movement of the shelves. The pipetting station may also include at least one pipette tip. The X-Y head an X-axis driver to move said pipette head linearly in an X direction parallel to said horizontal slot, to perform the pipetting, a Y-axis driver to move said pipette head linearly in a Y direction perpendicular to said X direction, to perform the pipetting function, wherein the X-axis driver and the Y-axis driver move said pipette tip to the container on said shelf, and the Z-axis driver moves the pipette tip into and out of said container. In some embodiments the X-axis driver and Y-axis driver each have an integral composition.

The pipetting station may be controlled in some embodiments by a personal computer, and may have an identification system is mounted on said X-Y head to read an identification tag attached to the container. The identification system may be a barcode reader to read barcodes.

In other aspects, the invention relates to a pipetting station for transferring liquid from one container to another to perform a protocol, comprising a means for holding a container of liquid, a means for raising and lowering said means for holding, a means for driving the means for holding, a means for aspirating and dispensing liquid into and out of the container, a means moving the means for aspirating and dispensing liquid, and a means for controlling, wherein said means for controlling selectively engages said means for holding, means for raising and lowering, means for driving, means for moving, and means for aspirating to perform the protocol.

In some aspects, the invention relates to a method of performing a pipetting operation of a liquid in a biotechnological protocol comprising the steps of providing a pipetting station having a back plate having at least one horizontal slot and at least one vertical slot, at least one substantially horizontally movable shelf, said shelf being movably attached to said back plate in a cantilever fashion, said shelf being functionally associated with said horizontal slot, said shelf adapted to receive a container having cavities to hold said liquid, a shelf driving means functionally associated with said shelf to move said shelf in a horizontal direction along said horizontal slot, said shelf having a home position and a center position along the horizontal slot, an X-Y head being movably attached to said at least one vertical slot in said back plate, a modular pipette head attached to said X-Y head functionally adapted to aspirate and dispense liquid into and out of said container, a Z-axis driving means functionally associated with said back plate and said X-Y head to move said X-Y head in a vertical direction, and a control system being functionally associated with said shelf driving means to selectively engage said shelf driving means, the control system selectively engaging said Z-axis driving means to move said X-Y head in a vertical direction, wherein said control system controls said shelf and said X-Y head to cooperatively move to perform said protocol, moving the shelf to a center location directly under said pipetting head, lowering said pipetting head into said container, aspirating the liquid into said container, raising said pipetting head; and returning the shelf to its home position. This method may include repeating the step of aspirating of said liquid into all of said cavities in said container, or providing a barcode reader mounted on the X-Y head, said container having a barcode, and scanning said barcode with the barcode reader.

In other embodiments, a method is described for transferring liquid by a robotic translation system from a first container holding a first volume of liquid to a second container holding a second volume of liquid comprising providing a pipetting station having a back plate having at least one horizontal slot and at least one vertical slot, at least one substantially horizontally movable shelf said shelf being movably attached to said back plate in a cantilever fashion, said shelf being functionally associated with said horizontal slot, said shelf adapted to receive a container to hold said liquid, a shelf driving means functionally associated with said shelf to move said shelf in a horizontal direction along said horizontal slot, an X-Y head being movably attached to said at least one vertical slot in said back plate, a modular pipette head attached to said X-Y head functionally adapted to aspirate and dispense liquid into and out of said container, a Z-axis driving means functionally associated with said back plate and said X-Y head to move said X-Y head in a vertical direction, and a control system being functionally associated with said shelf driving means to selectively engage said shelf driving means, the control system selectively engaging said Z-axis driving means to move said X-Y head in a vertical direction, wherein said control system controls said shelf and said X-Y head to cooperatively move to perform said protocol, and operating the control to manipulate the shelves and the pipetting head to transfer liquid from one container on a shelf to another container on a shelf.

Figure 1:
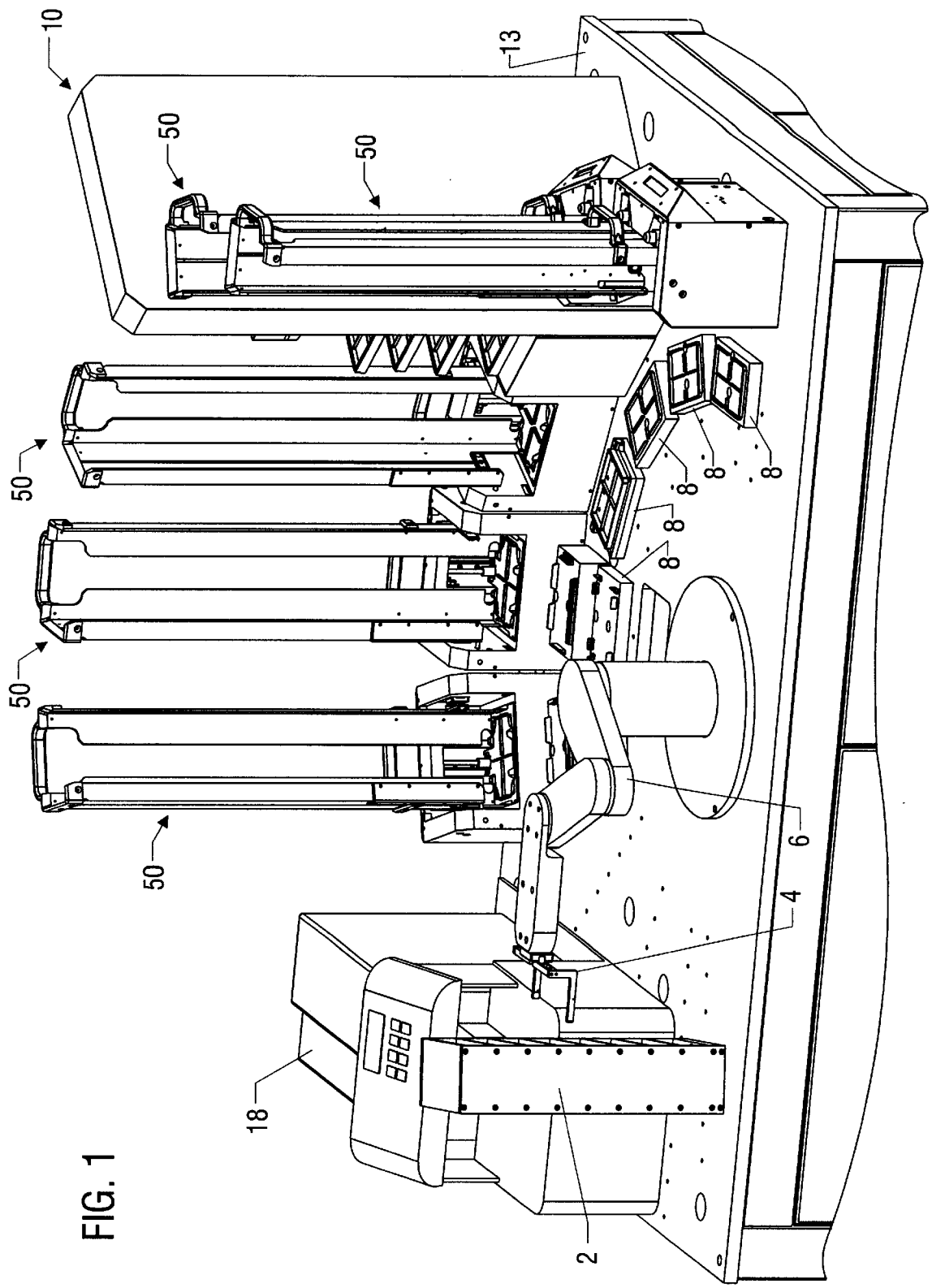
FIG. 1 shows an embodiment of the present invention as used in a complete system for performing protocols.

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents, and alternatives falling within the spirit and scope of the invention as defined by the appended claims.

DESCRIPTION OF ILLUSTRATIVE EMBODIMENTS

Illustrative embodiments will now be described with reference to the accompanying figures.

The invention relates to an apparatus and a method to increase the throughput of manipulating microwell plates when performing a pipetting operation. The invention increases throughput while reducing the size of the machine. The invention also improves the accuracy of the pipetting operation while also improving quality control. Further aspects and advantages of the invention will become apparent from consideration of the following description and drawings.

Referring now to FIG. 1, a system is shown for performing various sample analysis protocols. In this embodiment, modules of an automatic laboratory system are placed on table 13. Five plate stackers 50 are shown, although any number of stackers required for a particular protocol can be used. These stackers are used to store microwell plates as described in copending U.S. patent application Ser. No. 09/303,381 U.S. Pat. No. 6,193,102 entitled "Plate Stacker Apparatus" by Bevirt and Brinton filed on Apr. 20, 1999, issued on Feb. 27, 2001 incorporated by reference in its entirety herein. After stacker 50 prepares a microwell plate for presentation, holder 4 on robot arm 6 is directed to that stacker to lift that microwell plate from stacker 50. At that point, the robot arm 6 can carry the microwell plate to a pipetting station 10 to dispense small amounts of liquid. Or the robot arm 6 can carry the microwell plate to hotel 2. Hotel 2 can be a heating station. For instance, in some sample analyses, it is required to combine reagents in a controlled environment at a particular temperature which is above ambient temperature. In these instances, hotel 2 acts as an oven in which this reaction may occur.

Hotel 2 could also possess light detectors. In this way, if clear microwell plates were utilized, light could shine one side of the microwell plate in the hotel. Detectors could reside on the hotel positioned on the other side of the microwell plate. These detectors could then determine, for example, the color of the sample in each cavity of the microwell plates.

Hotel 2 could be replaced by any number of components to perform operations needed in a given protocol such as a wash station for a pipette, or stations for mixing, incubating, separating, and the like.

Alternatively, robot arm 6 can carry the microwell plate to the various resting stations 8. Any number of procedures could be performed in this fashion. A barcoding station could be placed on table 13 to barcode the microwell plates. Or a plate washing cell could be placed on table 13. Any number of steps in a biological protocol could be performed. Once one particular microwell plate has had all the steps performed as required by protocol, robot arm 60 can return the microwell plate to a stacker. Once all the microwell plates have gone through the protocol and are returned to a stacker 50, an operator (not shown) can remove the rack from the stacker 50 and take the rack of completed microwell plates to another area for post-processing as required.

Controller 18 coordinates the operation of the robot, the stacker, the pipetting station, and other modules to perform the desired protocols. Controller 18 can be any commercially available programming system, such a personal computer with appropriate software, which is readily known to one of ordinary skill in the art.

Figure 2A:
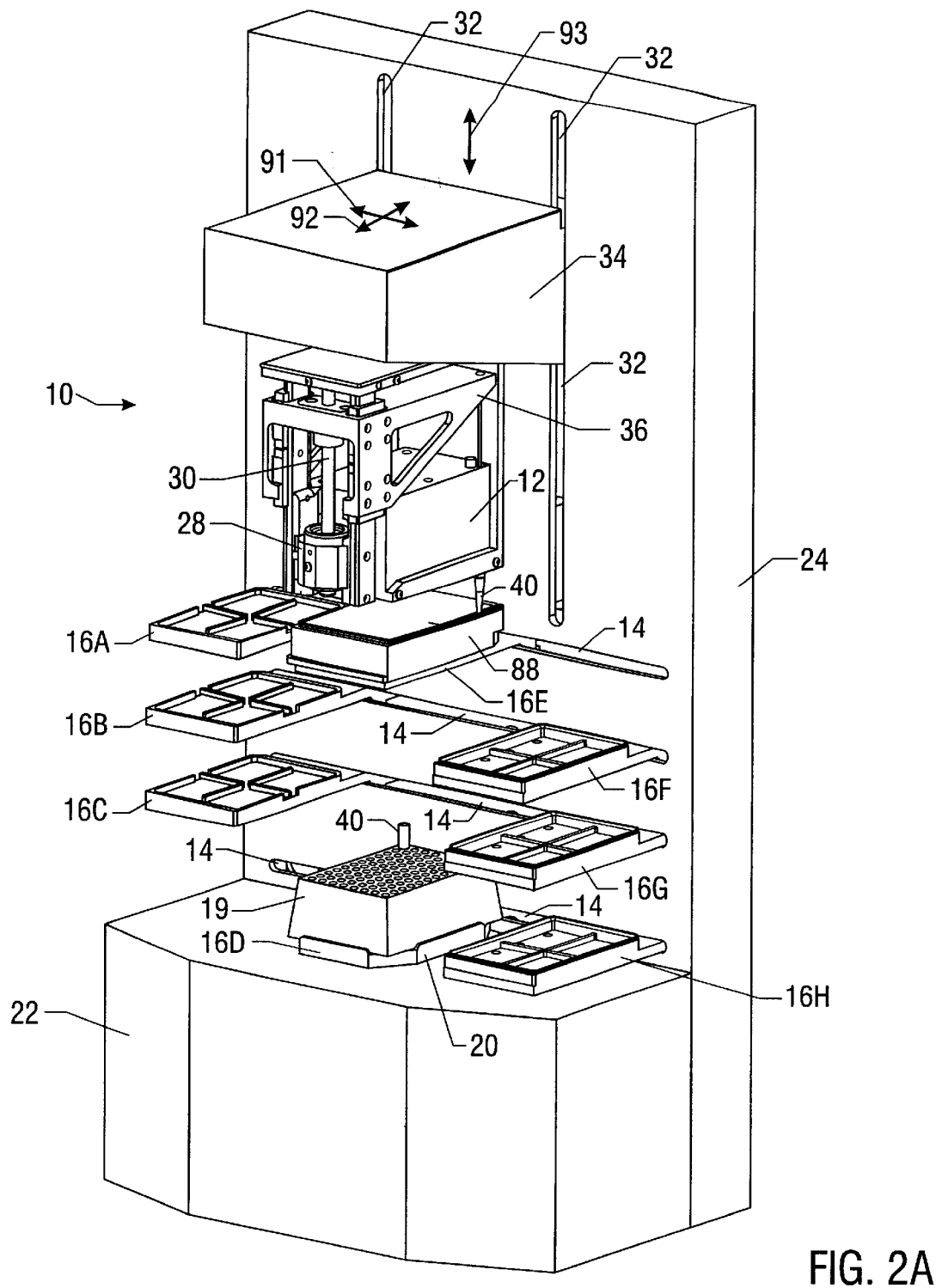
FIG. 2A illustrates one embodiment of a pipetting station of the present invention.

FIG. 2A shows a pipetting station 10. Pipetting station 10 is a device for measuring and transporting fluids from one microwell plate to another. In some embodiments pipetting station 10 has a small footprint of 9.75 inches by 15 inches. This small footprint improves the efficient integration of the pipetting station 10 into other robotic systems where robot accessible space is minimal. Pipetting station 10 has four axes of closed-loop sevo motor control including the control of pipette head 12.

Shown in FIG. 2A is pipetting station 10 having a base 22 and a back plate 24. Located on base 22 is pipette tip box press table 20. Located in pipetting tip box press table 20 is pipette tip box 19. Located in pipette tip box 19 is one pipette tip 40. As can be seen pipette tip box 19 is comprised of a matrix of cavities capable of accepting multiple pipette tips 40.

Located on back plate 24 are shelves 16A–16H for holding microwell plates, rinsing stations, and/or pipette heads. As can be seen in this embodiment, pipetting station 10 is capable of having eight different shelves 16. Thus, this multiple-plate system enables eight plates to be held at any given time. This significantly increases the capacity of pipetting station 10 over other pipetting stations on the market which stack plates side by side, and also allows a much more compact design. It should be noted that shelves 16A–16H may be simple cantilever shelves, or can include an alignment apparatus such as that disclosed in U.S. patent application Ser. No. 09/183,776, filed Oct. 30, 1998, entitled "Alignment Mechanism" by Bevirt, Brinton, and Lachenmeier, incorporated in its entirely herein.

Shelves 16A–16H can be pneumatically driven to move in X direction 91 along four, horizontally parallel slots 14. Pneumatics (not shown) drive shelves 16A–16H in the X direction via slot 14. Shelves 16A–16H are attached to slots 14 in a cantilever fashion.

In this embodiment, back plate 24 also contains two vertical parallel Z slots 32. Z slots 32 allow for movement of X-Y head 34 in Z direction 93. Mounted on X-Y head 34 is pipette head bracket 36. Mounted on pipette head bracket 36 is any type of modular pipette head 12. In this example, pipette head 12 is a modular system comprised of a pipette ball screw 30, an integrated motor housing 28, and pipette tip 40, although other types of pipette heads may be utilized.

X-Y head 34 can move in the Z direction via slots 32 in conjunction with closed loop sevo motors (not shown). X-Y head 34 also allows for motion of pipette head 12 in the X direction 91 and Y direction 92, again by closed loop servo motors (not shown). In some embodiments X-Y head 34 may move 9.5 inches in Z direction 93, 3.5 inches in the X direction 91, and 5.5 inches in the Y direction 92. This compact, modular approach allows the pipetting head 12 to carry several different kinds of heads and access eight plates on shelves 16. This allows great flexibility in the functions that the pipetting station 10 can accommodate.

Shelves 16A–16H are pneumatically driven with precision and accuracy. In operation a shelf 16 is presented to X-Y head 34 in a way such that any given number of protocols may be completed. A pipette station controller 90 (not shown) coordinates the movement of the pneumatic shelves in the X direction 91, the X-Y head in X-direction 91, Y direction 92, and Z direction 93 to perform the pipetting operation on the desired microwell tray for a given protocol. It should be noted that while one shelf is presented to the center X location for pipetting, other operations may be performed on the microwell trays on the other shelves. For instance, a robot arm could remove a microwell plate from shelf 16A while shelf 16B was being pipetted. This inherent multitasking feature of these embodiments of the present invention is advantageous since it allows for faster processing of biotechnological protocols.

In FIG. 2A, shelves 16 have been labeled 16A through 16H. Also, alignment mechanism 88 is clearly shown on shelf 16E. Shelves 16A–16H are stationary at either (1) a center location, or (2) an outer position along the X-axis 91. In FIG. 2A shelves 16E and 16D are in a center position along its X-axis 91. Furthermore, shelves 16A, 16B, 16C, 16F, 16G and 16H are in their outermost position along the X-axis 91.

Pipette station controller 90 (not shown) coordinates the movement of the shelves and the pipette head to perform a given series of pipetting operations. For example, in some embodiments, the pipetting station 10 could perform the following Example Sequence: (1) Take liquid out of microwell plate 16B, (2) insert liquid into the microwell plate of 16G, then (3) rinse the pipette tips.

To perform this Example Sequence, all shelves 16A–16H start in their outermost position along X-axis 91 and X-Y head 34 is in its uppermost position along Z-axis 93. Pipette tip box 18 is placed in shelf 16D. In this example, pipette tip box 18 contains 96 pipette heads 40. Further, a washing station is placed on shelf 16F and microwell plates are placed in the remaining shelves.

In the Example Sequence, shelf 16D is pneumatically driven to its center position along X-axis 91. X-Y head 34 moves downwardly in the Z direction until pipette head 12 comes into contact with the pipette tips 40. Pipette head 12 then connects to each pipette head 40. Once connected, pipette head 12 and X-Y head 34 move upwardly in the Z direction.

Shelf 16B then moves to the center position along its X-axis. X-Y head 34 then moves downwardly in the Z direction until pipette tips 40 are inserted into the microwell plate on tray 16B. Pipette head 12 then performs its pipetting operation from the cavities of microwell plate on shelf 16B. Once the pipetting operation is completed, X-Y head 34 moves upwardly in a Z direction thus removing pipette tips 40 from the cavities of microwell plate. Shelf 16B then moves to its outermost position along the X-axis.

Then in the Example Sequence, shelf 16G moves to its centermost position along the X-axis. X-Y head 34 moves downwardly in the Z direction until pipette tips 40 are inserted into the microwell cavities on the microwell plate located on shelf 16G. Again a pipetting operation is performed into each microwell cavity as described above. Upon completion of the pipetting operation, X-Y head 34 moves upwardly in a Z direction and shelf 16G is pneumatically returned to its outermost position along the X-axis.

Shelf 16F next moves to its centermost location. X-Y head 34 moves downwardly in a Z direction until pipette tips 40 come in contact with the wash bath (not shown) placed on shelf 16F. X-Y head 34 then moves upwardly and shelf 16F is returned to its outermost position along X-axis 91, thus completing the Example Sequence.

In this way shelves can be manipulated and various pipetting operations may be performed until any given sequence is completed.

By having pipetting station 10 with shelves 16A–16H capable of independent manipulation, and by utilizing various pipetting heads, the microbiology protocols can be practiced in a flexible manner. This is a great advantage over prior art pipetting systems where either (1) conveyers are used and only one microwell plate can be processed in a given time—which increases the time of the pipetting operation—or (2) multiple microwell plates are placed side by side and spread out on a table—which increases the size of the pipetting apparatus. Because eight shelves 16A–16H are available and some are vertically stacked in this pipetting station 10, pipetting station 10 allows for more rapid completion of pipetting protocols. Further, because of this stacking arrangement of the shelves, the space the pipetting station requires in the laboratory is reduced. Finally, because of the method in which the shelves are presented to the pipetting system, multitasking of multiple operations simultaneously is possible.

Figure 2B:
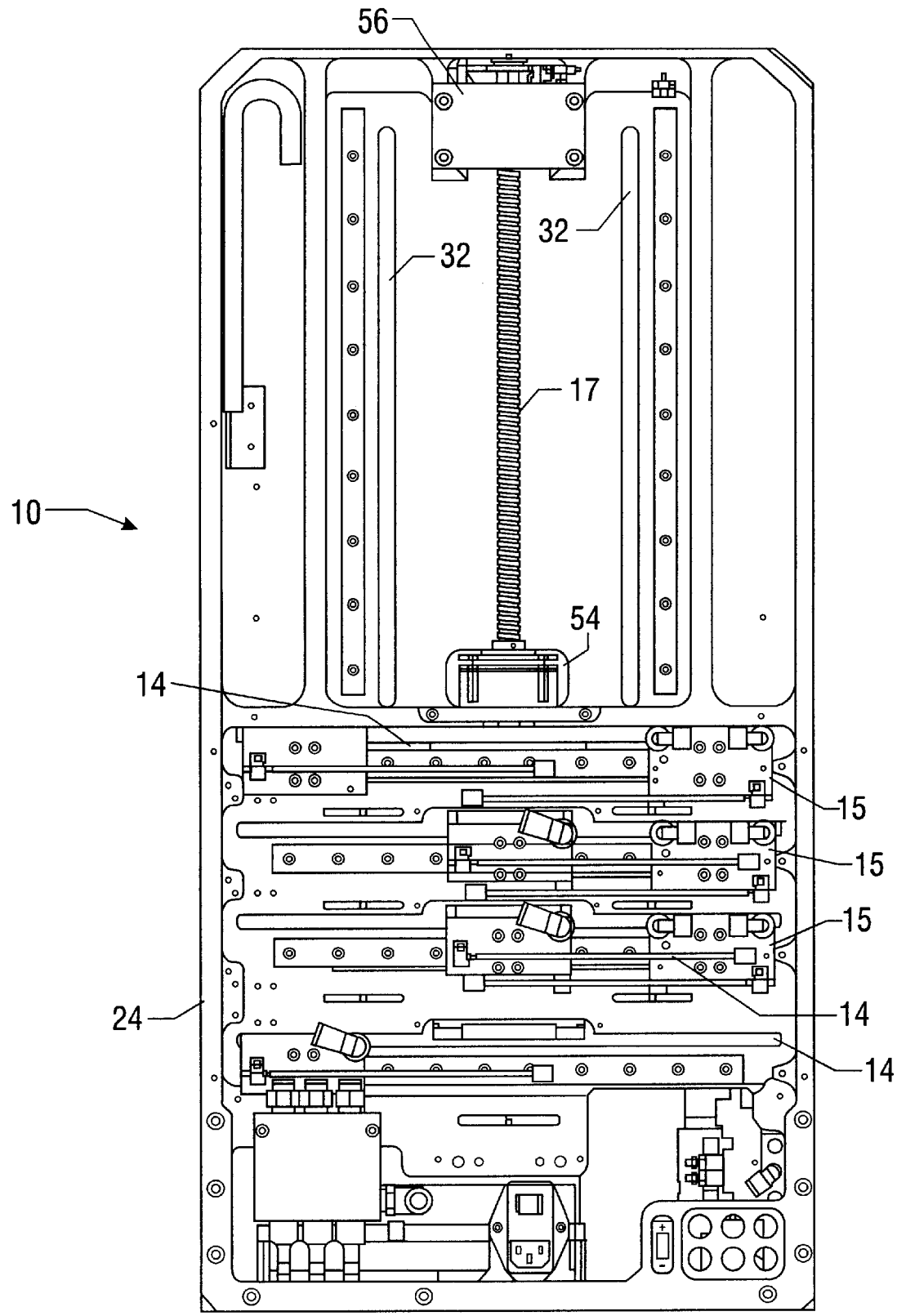
FIG. 2B shows a rear view of the embodiment shown in FIG. 2A.

FIG. 2B shows a rear view of the pipetting station shown in FIG. 2A. The four horizontally parallel shelf slots 14 are shown, as are the two vertically parallel Z slots 32. Also shown is Z drive ball screw 17, break 56 (covered), and stator 54. As will be described in conjunction with FIG. 4, the motor drive shaft including the bearing seats and encoder interface is machined from ball screw shaft 17. This integral design allows for more compact components and negligible backlash compared to conventional couplings gears, belts, or pulleys. This is because there is no coupling of the motor-shaft to the ball screw. The ball screw is integral with the motor shaft. A frameless, brushless DC motor is incorporated into the machine parts which also reduces the space required compared to mounting a motor. Further by the motor housing being integral to the system the motor is more secure and accurate compared to externally mounted motors.

Figure 2C:
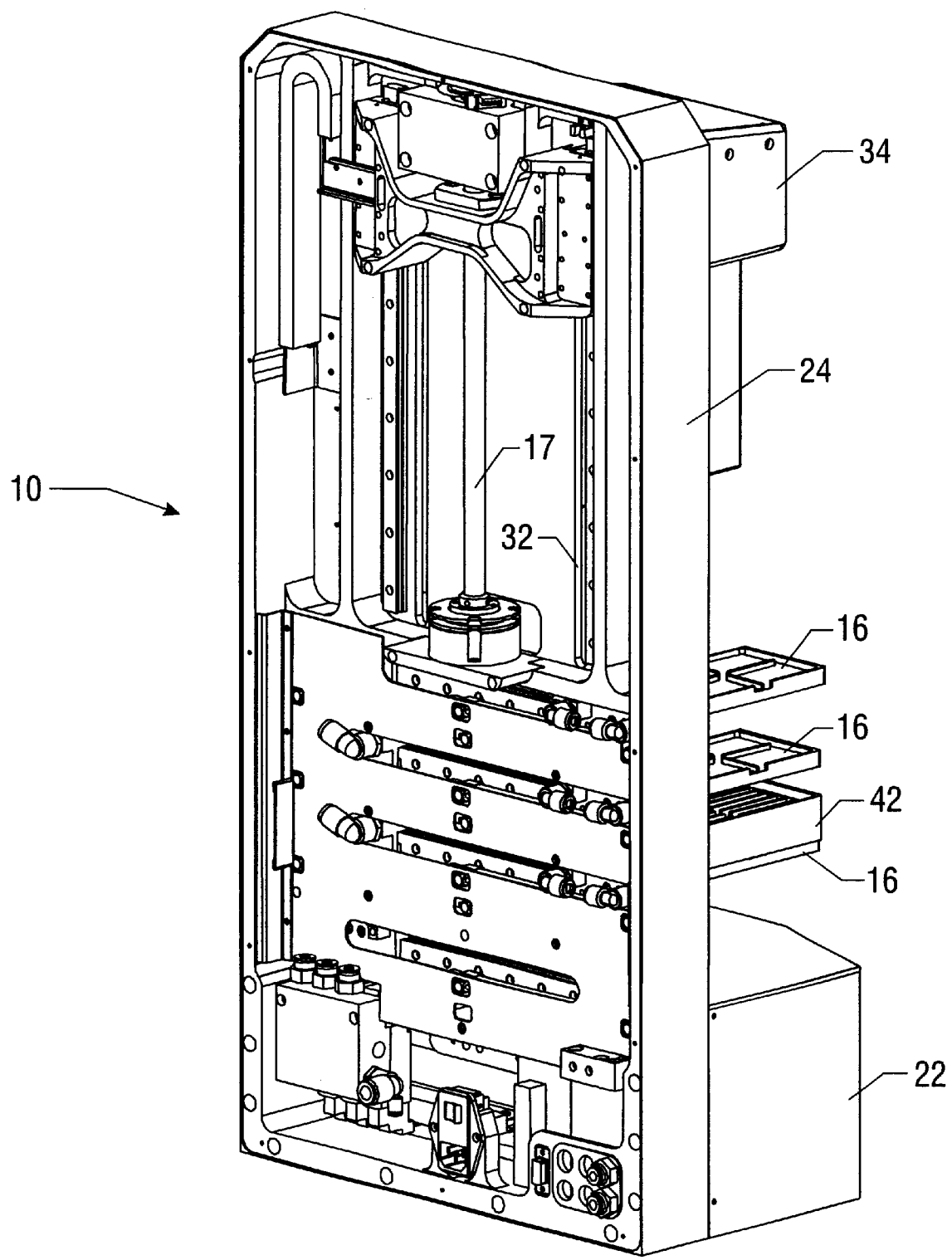
FIG. 2C shows another view of the embodiment shown in FIG. 2A.

FIG. 2C shows pipetting station 10 along with X-Y head 34, backplate 24, Z slot 32, Z ballscrew 17, shelves 16, and base 22.

Figure 2D:
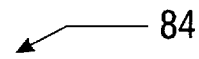
FIGS. 2D and 2E shows an industry standard 96-well microwell plate.
Figure 2E:

It should be noted that X-Y head 34 is also capable of moving the pipette tips 40 in the X direction 91 and Y direction 92 as previously discussed. Therefore, it is possible for a pipette head 12 containing twenty four (24) pipette tips 40 to be used to pipette into an industry standard 96 cavity microwell plate, by simply repeating the pipetting operation four times. For example, referring to FIG. 2D, an industry standard 96 well microwell plate 84 is shown having 12 rows (1–12) of 8 columns (A–H) of cavities. The pipette tips 40 can be configured on the pipette head 12 such that, when the pipette tips are inserted into the microwell cavities, every other cavity in the X and the Y direction is empty. For example, the 24 pipette tips 40 could be configured to align with the following cavities in microwell plate 84 of FIG. 2D: A1, C1, E1, and G1; A3, C3, E3, and G3; A5, C5, E5, and G5; etc. through rows 7, 9, and 11 as denoted by Xs in FIG. 2E. Once the pipetting operation is completed in these cavities, the first pipette tip (used to dispense into A1) could be used to pipette liquid into cavity B1, then B2, and finally A2, the other twenty three tips dispensing liquid into the other cavities in a similar fashion concurrently.

Of course, the same type of procedure could be utilized in any number of ways such as with one pipette tip 40 on pipette head 12 repeating pipetting operation 384 times for a 384 cavity microwell; or 96 tips 40 on pipette head 12 could be used on a 384 microwell plate by repeating the pipetting operation four times.

Figure 3A:
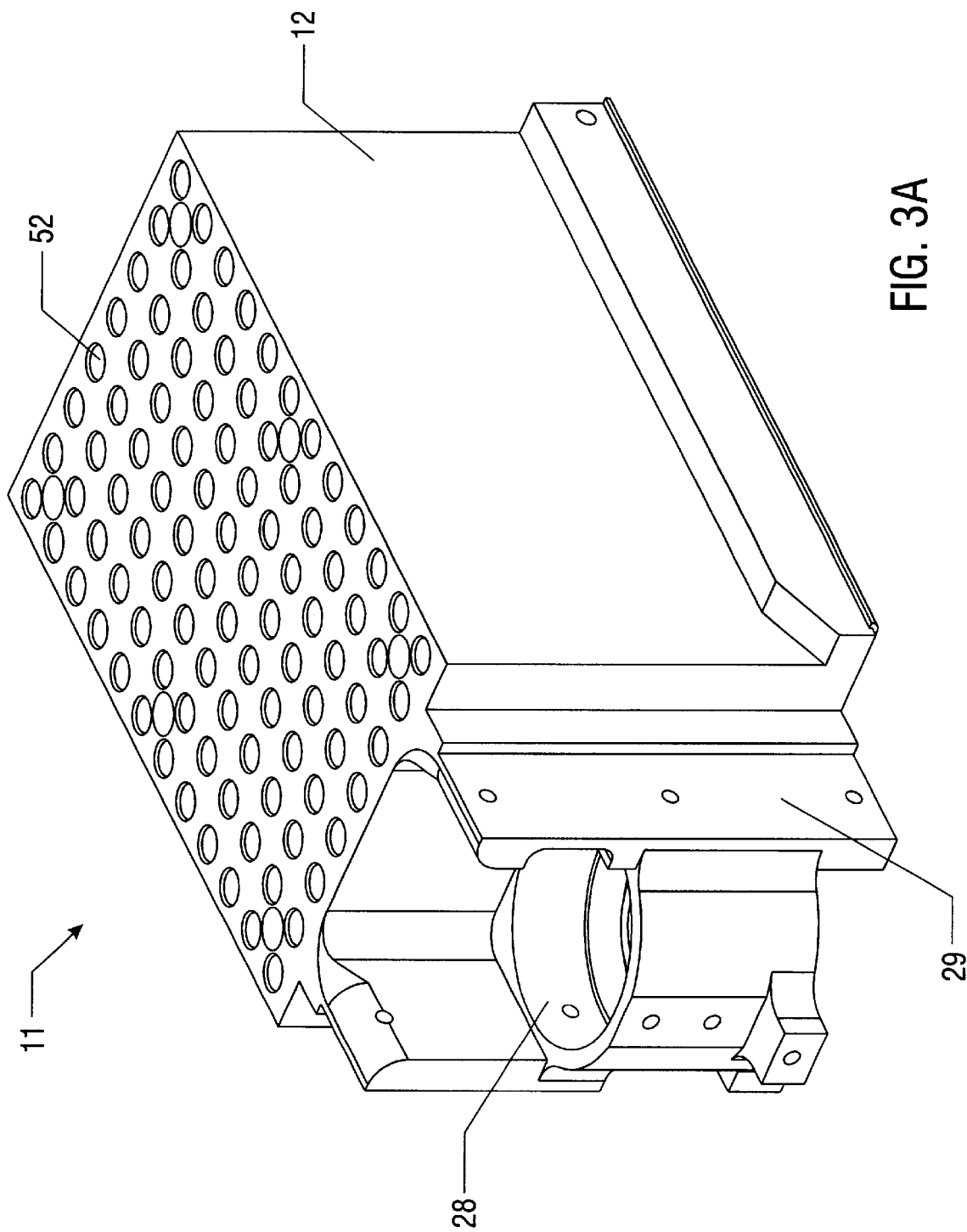
FIG. 3A shows a modular pipette head.

Referring to FIG. 3A, one example of a modular pipetting head 12 is shown. For instance, a pipetting head 12 is shown to be comprised of pipette head 12, integrated motor housing 28, and pipette head linear rail mount site 29. It is important to realize that this particular head—as disclosed in patent application Ser. No. 09/495,489 entitled "Multi Channel Pipette Head" by Bevirt and Guyot, concurrently filed with this application having attorney is only one type of modular pipetting head which can be used with this pipetting station 12. Any number of commercially available of pipetting heads could be used in this modular fashion.

Figure 3B:
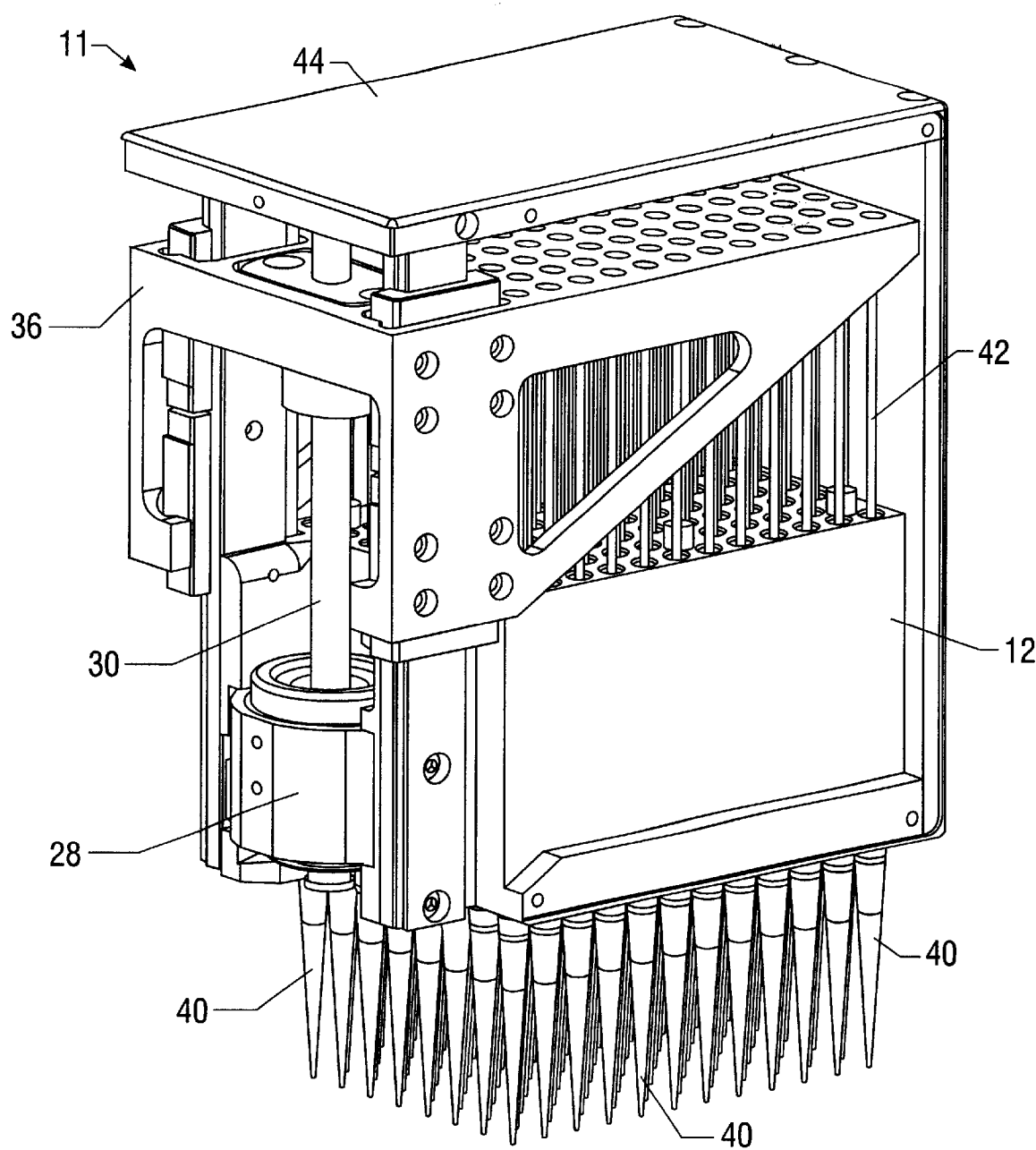
FIG. 3B shows the modular pipette head of FIG. 3A including pipette heads, and an integrated motor.

Referring to FIG. 3B, pipette head 12 is shown to include pipette head ball screw 30, pipette head bracket 37, pipette head cover 44, piston 42, and pump housing 12. Pipette tips 40 are also shown. The function of the pipette head is to transfer liquid in small quantities very accurately to and from microwell plates.

Figures 4, 5:
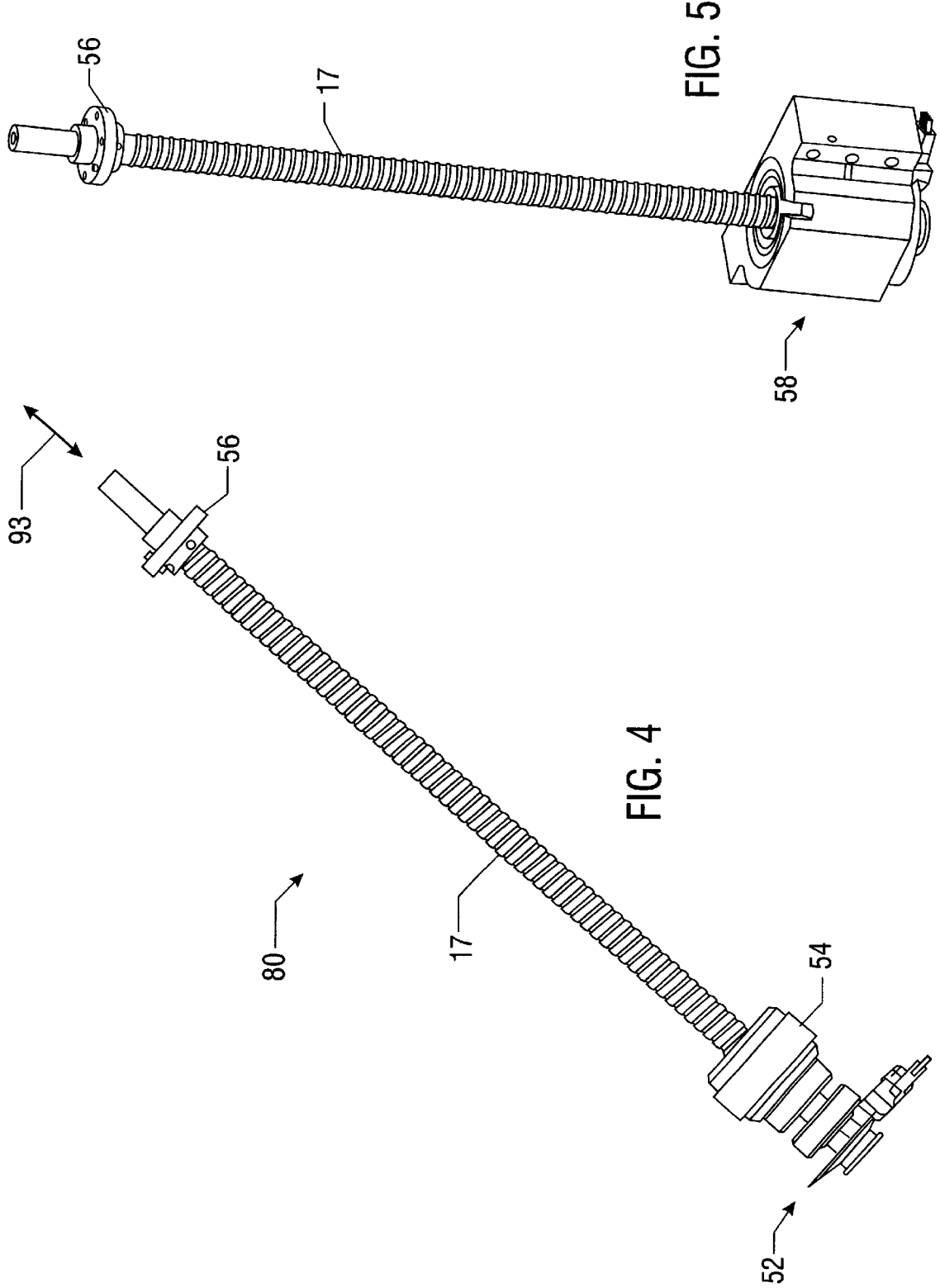
FIG. 4 illustrates an integrated Z-ball screw and motor shaft of an embodiment of the present invention.
FIG. 5 illustrates an integrated motor housing of one embodiment of the present invention.

Referring now to FIG. 4, integrated Z ball screw and motor shaft 80 is shown in an isolated fashion. Integrated Z ball screw and motor shaft 80 is shown to be comprised of encoder 52, stator 54, ballscrew 17, and break 56. FIG. 5 shows integrated motor housing 58 mounted on ballscrew 17. Shown in FIGS. 5, motor housing 58 surrounds encoder 52 and stator 54. Again it is advantageous to have the Z ball screw integral with the motor shaft thus reducing the requirement of having a coupling system to couple the motor shaft to the Z ball screw. In operation, stator 54 rotates ball screw 17 thus driving X-Y head 34 upwardly or downwardly along Z-axis 93. Break 56 is applied to stop X-Y head 34 at a proper location. Encoder 52 is used to determine accurately the orientation in the Z direction of the X-Y head 34.

Figure 6:
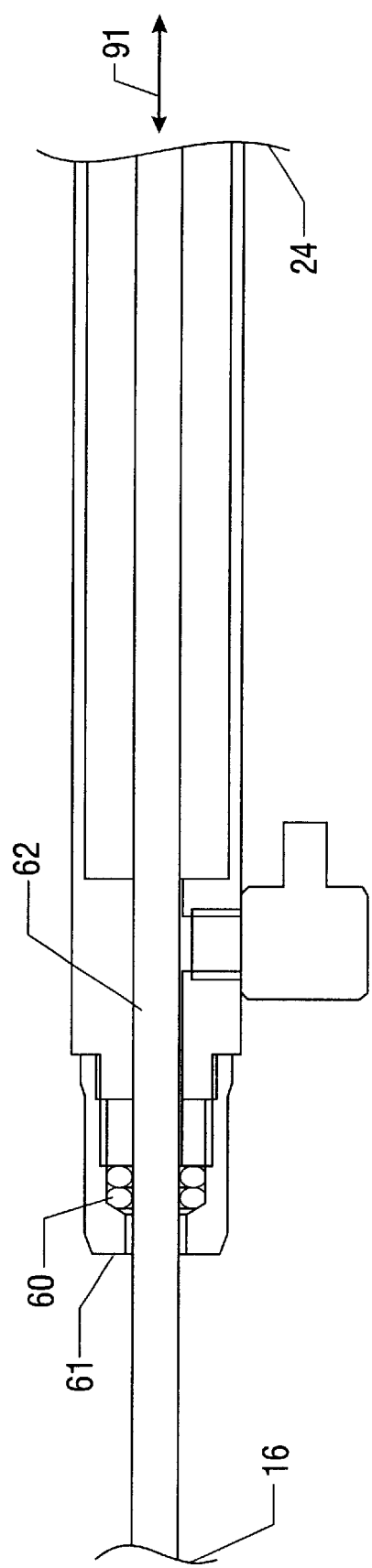
FIG. 6 illustrates components for pneumatic actuation of one embodiment of the present invention.

FIG. 6 shows compressed O-rings 60 and cylinder piston 62 used in conjunction with the pneumatic shelf-actuating system. Sliding shelves 16A–16H move in X direction 91 through shelf slot 14 as shown in FIG. 2A. In some embodiments this movement in the X direction 91 is provided via pneumatic actuation. To ensure a shelf 16 comes to a gradual stop when moving to the outermost X position, compressed O-rings 60 are provided surrounding cylinder piston 62. Cylinder piston 62 is attached to back plate 24 on one end, and shelf 16 on the other. End-of-travel springs (not shown) may also surround cylinder piston to provide gentle deceleration. End-of-travel springs may be attached in housing 61 surrounding O-rings 60 on one end, and near the back plate 24 on the other. Double O-rings 60 introduce damping into the system resulting in smooth, high-speed, low-cost microwell plate shuttling. The O-rings 60 and the end-of-travel springs (not shown) together give smooth, consistent motion from the pneumatic system. The pneumatic control is provided by any commercially available pneumatic system known to one of ordinary skill in the art.

Figure 7:
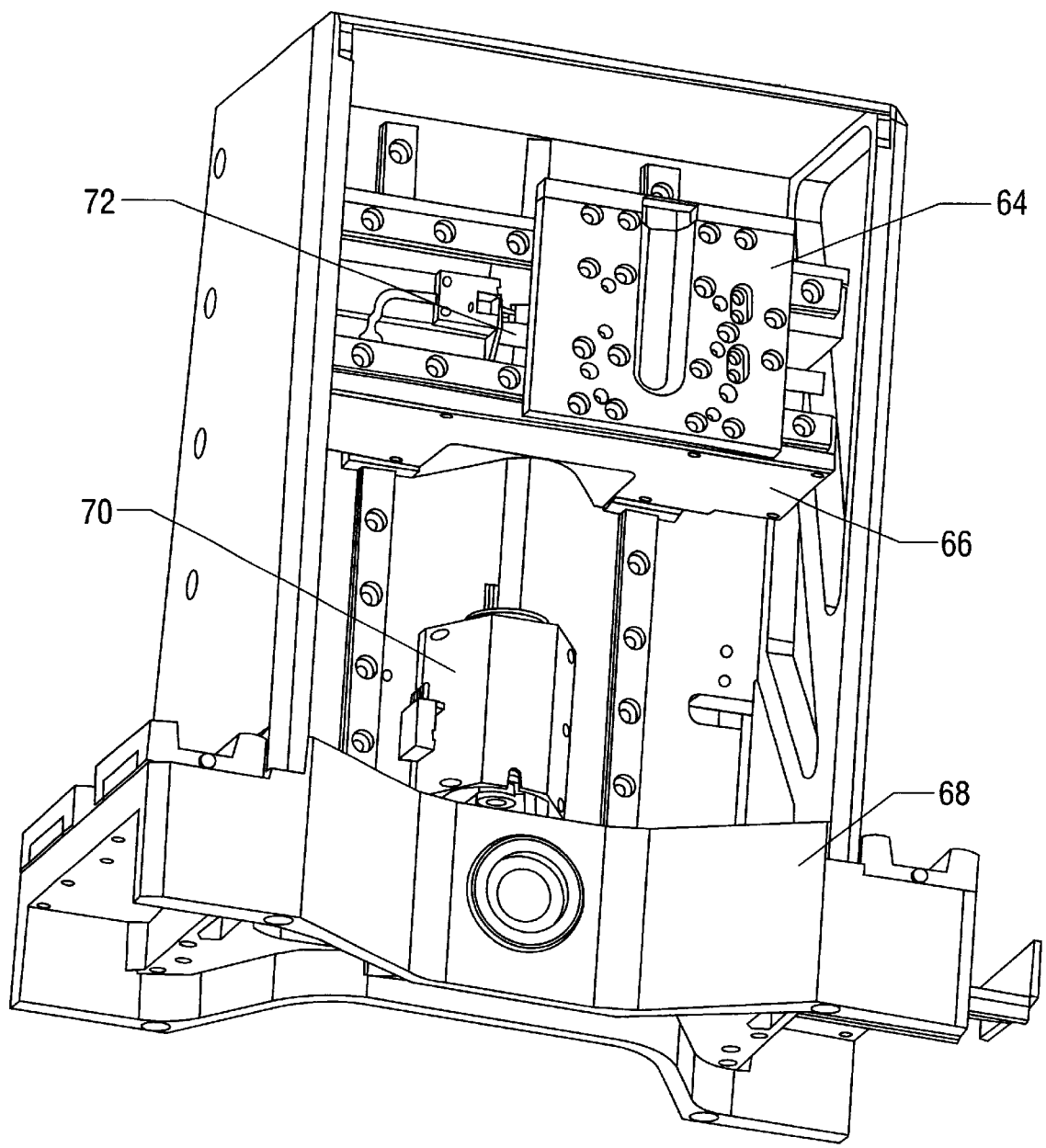
FIG. 7 illustrates an bottom view of an X-Y stage of one embodiment of the present invention.

FIG. 7 shows a bottom view of the X-Y stage of X-Y head 34. The X-Y stage is the mechanism by which X-Y head 34 travels in the X direction 91 and the Y direction 92 as shown in FIG. 2A. X stage 64 is driven by X servo motor 72 in the X direction. Y stage 66 is driven by Y servo motor 70 in the Y direction. Z stage 68 is driven by integrated Z ball screw and motor shaft 80 as described previously. In this embodiment, the mechanism driving both the X and Y stages are similar to that described above: the X and Y stages have an integrated drive ball screw in which encoder and stator are all integral with the motor shaft. Again, as discussed above regarding FIG. 4, the integrated ball screw allows for compact design, reduces backlash, and increases system accuracy. Frameless motors integrated into the lead screw and motor shaft combination allows for a compact design. These reduce space and increase reliability accuracy and speed in the X-Y direction. Pipette stations controller 90 (not shown) coordinates the engagement of X and Y servo motors.

Figure 8:
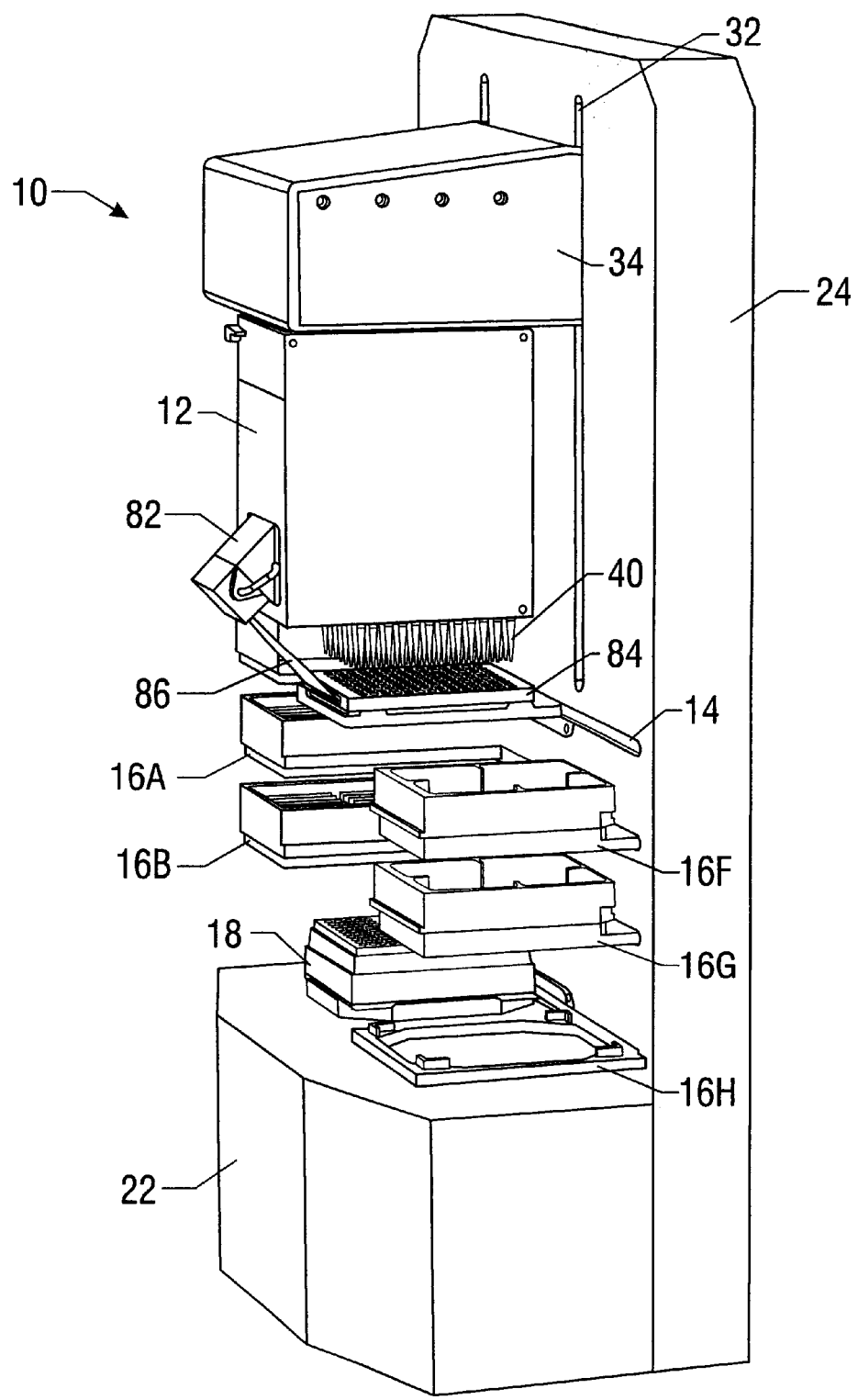
FIG. 8 shows an embodiment of the present invention including a barcode reader.

FIG. 8 shows an embodiment of the present invention in which pipetting station 10, as shown in FIG. 2A, is equipped with barcode reader 82. A similar barcode reading system is described in the U.S. patent application Ser. No. 09/496,100 by Bevirt and Brinton entitled "Robot Mounted Barcode Reader" filed concurrently with this application having herein incorporated by reference in its entirety. Also clearly shown in FIG. 8 is microwell plate 84.

FIG. 8 shows a laser barcode reader 82 mounted on modular pipette head 12. Barcode reader 82 is small enough to be mounted on pipette head 12 without adding excess weight which could decrease the accuracy of the pipetting operation. In one embodiment, the dimensions of barcode reader 82 are three inches by four inches by two inches. Small laser barcode readers that can readily be mounted on pipette head 12 are commercially available from Microscan or other barcode reader manufactures. For instance, Microscan model MS-310 may be used. Alternatively, other object identification systems may be used including, but not limited to, CCD, 2-dimensional scanner, wand scanners, and magstripe readers. The invention is thus not limited to the laser barcode reader disclosed: any identification system known to those of skill in the art may be used. In each of the alternative identification systems, the associated tags and graphics to be detected and read will be in incorporated onto the microwell plate. It is within the ordinary skill of one in the art to find and purchase such systems and tags.

In operation, prior to initiating the pipetting operation, a shelf 16 is presented under pipette head 12. Barcode reader 82 is mounted to pipette head 12 such that the barcode reader 86 is at an angle creating a clear line of site between barcode reader 86 and microwell plate 84. A laser line projection 86 is shown in FIG. 8 illustrating the clear line of sight that is advantageous between the barcode reader 82 and microwell plate 84. After scanning the barcode on the microwell plate, the information gathered from the barcode is returned to pipette station controller 90 for processing. In this way, the quality control of the pipetting operation is improved: if the wrong microwell plate was inadvertently placed in the pipetting station, pipette controller 88 could cease the pipetting operation once the barcode was scanned and the mistake was discovered.

Previous pipetting stations have the motor shaft coupled in some way to the ball screw. This increases the size of the components, and can allow some play between the motor shaft and the ball screw. This is space-consuming and inaccurate compared to the integral system described above. The embodiments described above for movement in the X, Y, and Z directions alleviate the need to couple the motor shaft to the ball screw.

Because prior pipetting systems cannot handle eight different shelves of microwell plates in a compact area, their utilization in small environments is limited. However, because this embodiment includes multiple shelves 16A–16H, multitasking operations are possible. This compact design allows for significant savings of space in the work area.

The appended claims are intended to cover all such modifications and variations not limited to the specific embodiments which occur to one of ordinary skill in the art; the claims are not limited to the specific embodiments earlier described.

Although various embodiments have been shown and described, the invention is not so limited and will be understood to include all such modifications and variations as would be apparent to one skilled in the art.

The following table lists the description and the numbers as used herein and in the drawings attached hereto.

2 Hotel
4 Holder
6 Robot Arm
8 Resting Stations
10 Pipetting Station
12 Pipette head
13 Table
15 Sliding Shelve Attachment
16 Shelf
17 Z-drive ball screw
18 Controller
19 Pipette Tip Box
20 Pipette Tip Box Press Table
22 Base
24 Back Plate
28 Integrated Motor Housing
28 Integrated Motor Housing on Pipette Head
29 Pipette Head Linear Rail Mount Site
30 Pipette Head Ball Screw
32 Z-slot
34 X-Y head
36 Pipette Head Bracket
40 Pipette Tip
44 Pipette Head Cover
50 Plate Stacker
52 Encoder
54 Stator
56 Brake
58 Integrated Z motor housing
60 O-rings
61 Housing
62 Cylinder Piston
64 X-stage
66 Y-stage
68 Z-stage
70 Y-motor
72 X-motor
80 Integrated Z-ball screw and motor shaft
82 Barcode reader
84 Microwell plate
86 Laser line projection
88 Alignment Mechanism
90 Pipette Station Controller
91 X-axis
92 Y-axis
93 Z-axis

What is claimed is:

1. A pipetting station for transferring liquid from one container to another to perform a protocol, comprising:
   a back plate having at least one horizontal slot and at least one vertical slot;
   at least one substantially horizontally movable shelf,
      said shelf being movably attached to said back plate in a cantilever fashion;
      said shelf being functionally associated with said horizontal slot;
      said shelf adapted to receive a container to hold said liquid;
   a shelf driving means functionally associated with said shelf to move
      said shelf in a horizontal direction along said horizontal slot;
   an X-Y head being movably associated with said at least one vertical slot in said back plate;
   a modular pipette head attached to said X-Y head functionally adapted to aspirate and dispense liquid into and out of said container;
   a Z-axis driving means functionally associated with said backplate and said X-Y head to move said X-Y head in a vertical direction; and
   a control system being functionally associated with said shelf driving means to selectively engage said shelf driving means;
      the control system selectively engaging said Z-axis driving means to move said X-Y head in a vertical direction,
   wherein said control system controls said shelf and said X-Y head to cooperatively move to perform said protocol.

2. The pipetting station of claim 1 in which the Z-axis driving means further comprises:
   a Z-drive ball screw having a first end and a second end;
   a brake attached to said first end of the Z-drive ball screw;
   a stator integrally attached to said back plate and functionally adapted to receive said second end of said Z-drive ball screw;
   an encoder integrally attached to said second end of the Z-drive ball screw; and
   a motor to rotate the Z-drive ball screw within the stator relative to the back plate.

3. The pipetting station of claim 1 in which the shelf driving means is a pneumatic actuator.

4. The pipetting station of claim 3 further comprising:
   a cylinder piston having a first end and a second end,
      said first end connect to said shelf,
      said second end connected to said back plate;
   at least one O-ring surrounding said cylinder piston;
   at least one first end-of-travel spring being functionally associated with each said shelf; and
   at least one second end-of-travel spring being functionally associated with said second end of said cylinder piston,
      said end-of-travel springs dampening the horizontal movement of said shelf as
      said shelf approaches an end of said horizontal slot,
      said O-rings providing damping to horizontal movement of said shelf along a length of cylinder piston.

5. The pipetting station of claim 1 in which the pipette head further comprises at least one pipette tip.

6. The pipetting station of claim 5 in which the X-Y head further comprises:

an X-axis driver to move said pipette head linearly in an X direction parallel to said horizontal slot, to perform the pipetting; and a Y-axis driver to move said pipette head linearly in a Y direction perpendicular to said X direction, to perform the pipetting function, wherein the X-axis driver and the Y-axis driver move said pipette tip to the container on said shelf,
said Z-axis driving means moving said pipette tip into and out of said container.

7. The pipetting station of claim 6 in which said X-axis driver further comprises:

an X-drive ball screw having an end;
a motor housing integrally formed with said X-Y head, said motor housing adapted to receive the first end of said X-drive ball screw; and
a servo motor to rotate said X-drive ball screw within said motor housing,
wherein when X-drive ball screw rotates, said pipette head is moved in the X direction.

8. The pipetting station of claim 7 in which said Y-axis driver further comprises:

a Y-drive ball screw having an end;
a motor housing integrally formed with said X-Y head, said motor housing adapted to receive the first end of said Y-drive ball screw; and
a servo motor to rotate said Y-drive ball screw within said motor housing,
wherein when Y-drive ball screw rotates, said pipette head is moved in the Y direction.

9. The pipetting station of claim 1 wherein the controller is a personal computer.

10. The pipetting station of claim 1 in which an identification system is mounted on said X-Y head to read an identification tag attached to the container.

11. The pipetting station of claim 10 in which an identification system is a barcode reader and the identification tag is a barcode.

12. A pipetting station for transferring liquid from one container to another to perform a protocol, comprising:

a back plate having four horizontal slots and two vertical slots;
eight horizontally movable shelves,
each said shelf being movably associated to said back plate in a cantilever fashion;
two of said shelves being functionally associated with each horizontal slot;
said shelves adapted to receive a microwell plate to hold said liquid;
a pneumatic shelf driving means functionally associated with each of said shelves to selectively move each said shelf in a horizontal direction along the horizontal slot,
eight cylinder pistons, each cylinder having a first end and a second end,
each said first end of said cylinder piston being connected to a shelf and each said second end of said cylinder piston being connected to the backplate,
eight pairs of O-rings, each said pair of O-rings surrounding said cylinder piston;
eight first end-of-travel springs, each first end-of-travel spring being functionally associated with each shelf;
eight end-of-travel springs, each being functionally associated with each said second end of said cylinder piston,
said end-of-travel springs dampening the horizontal movement of said shelf as said shelf travels reaches an extent of horizontal motion,
said O-rings providing damping of the horizontal movement of said shelf along a length of said cylinder piston;

an X-Y head being movably attached to said the vertical slots in said back plate;
a modular pipette head having 96 pipette tips, being attached to said X-Y head, for aspirating and dispensing liquid into and out of said container;
said X-Y head having an X-drive ball screw having an end, to move said pipette head linearly in an X direction parallel to said horizontal slots,
said X-Y head having a Y-drive ball screw having an end to move said pipette head linearly in a Y direction perpendicular to said X direction;
a motor housing integrally formed with said X-Y head, said motor housing adapted to receive the end of said X-drive ball screw;
a first servo motor to rotate said X-drive ball screw within said motor housing,
wherein when X-drive ball screw rotates, said pipette head is moved in the X direction,
wherein the X-axis drive ball screw and the Y-axis drive ball screw move said pipette tips into and out of said container;
a motor housing integrally formed with said X-Y head, said motor housing adapted to receive the end of said Y-drive ball screw;
a second servo motor to rotate said Y-drive ball screw within said motor housing,
wherein when Y-drive ball screw rotates, said pipette head is moved in the Y direction;
a barcode reader mounted on said X-Y head to scan a barcode attached to the container;
a Z-drive ball screw having a first end and a second end and being functionally associated with said back plate and said X-Y head to move said X-Y head in a vertical direction;
a brake attached to said first end of the Z-drive ball screw;
a stator housing integrally attached to said back plate and functionally adapted to receive said second end of said Z-drive ball screw;
an encoder integrally attached to said second end of the Z-drive ball screw;
a motor to rotate the Z-drive ball screw within the stator relative to the back plate, said motor being integral with said back plate; and
a personal computer being functionally associated with said pneumatic shelf driving means to selectively engage said pneumatic shelf driving means;
the computer selectively engaging said Z-axis drive ball screw to move said X-Y head in the vertical direction,
wherein said computer controls said shelves and said X-Y head to cooperatively move to perform said protocol.

13. A method of performing a pipetting operation of a liquid in a biotechnological protocol comprising the steps of:

providing a pipetting station having a back plate having at least one horizontal slot and at least one vertical slot,
at least one substantially horizontally movable shelf,
said shelf being movably attached to said back plate in a cantilever fashion,
said shelf being functionally associated with said horizontal slot, said shelf adapted to receive a container having cavities to hold said liquid,
a shelf driving means functionally associated with said shelf to move
said shelf in a horizontal direction alone said horizontal slot,
said shelf having a home position and a center position along the horizontal slot,
an X-Y head being movably attached to said at least one vertical slot in said back plate,
a modular pipette head attached to said X-Y head functionally adapted to aspirate and dispense liquid into and out of said container,
a Z-axis driving means functionally associated with said back plate and said X-Y head to move said X-Y head in a vertical direction, and
a control system being functionally associated with said shelf driving means to selectively engage said shelf driving means,
the control system selectively engaging said Z-axis driving means to move said X-Y head in a vertical direction,
wherein said control system controls said shelf and said X-Y head to cooperatively move to perform said protocol;
moving the shelf to a center location directly under said pipetting head;
lowering said pipetting head into said container;
aspirating the liquid into said container;
raising said pipetting head; and
returning the shelf to its home position.

14. The method of claim 13 further comprising:
repeating the step of aspirating of said liquid into all of said cavities in said container.

15. The method of claim 13 further comprising:
providing a barcode reader mounted on the X-Y head, said container having a barcode; and
scanning said barcode with the barcode reader.

16. A method for transferring liquid by a robotic translation system from a first container holding a first volume of liquid to a second container holding a second volume of liquid comprising:
providing a pipetting station having
a back plate having at least one horizontal slot and at least one vertical slot,
at least one substantially horizontally movable shelf,
said shelf being movably attached to said back plate in a cantilever fashion,
said shelf being functionally associated with said horizontal slot,
said shelf adapted to receive a container to hold said liquid,
a shelf driving means functionally associated with said shelf to move
said shelf in a horizontal direction along said horizontal slot,
an X-Y head being movably attached to said at least one vertical slot in said back plate,
a modular pipette head attached to said X-Y head functionally adapted to aspirate and dispense liquid into and out of said container,
a Z-axis driving means functionally associated with said back plate and
said X-Y head to move said X-Y head in a vertical direction, and
a control system being functionally associated with said shelf driving means to selectively engage said shelf driving means,
the control system selectively engaging said Z-axis driving means to move said X-Y head in a vertical direction,
wherein said control system controls said shelf and said X-Y head to cooperatively move to perform said protocol; and
operating the control to manipulate the shelves and the pipetting head to transfer liquid from one container on a shelf to another container on a shelf.

17. The method of claim 16 further comprising:
providing a barcode reader mounted on the X-Y head, said container having a barcode; and
scanning said barcode with the barcode reader.

18. A presentation system for use with pipetting station having a first horizontal slot and a second horizontal slot parallel and below the first horizontal slot, comprising:
a first substantially horizontally movable shelf movably attached to the first horizontal slot;
a second substantially horizontally movable shelf movably attached to the second horizontal slot,
said second shelf being located vertically lower than said first shelf,
said first and second shelves being, movably attached to said first and second slots in a cantilever fashion;
said shelves adapted to receive a container to hold said liquid; and
a shelf driving means functionally associated with said first shelf to move said first shelf in a horizontal direction along said horizontal slot,
wherein when the pipetting station is pipetting the container in the first shelf, the container in the second shelf is accessible for a simultaneous operation.

19. The presentation system of claim 18 wherein said shelf driving means are pneumatics.

20. A pipetting station for transferring liquid from one container to another to perform a protocol, comprising:
a back plate;
a substantially horizontally movable shelf,
said shelf being movably attached to the back plate,
said shelf adapted to receive a container to hold said liquid;
a shelf driving means functionally associated with the shelf to move the shelf in a horizontal direction;
an X-Y head being movably associated with the back plate, the X-Y head having at least one pipette functionally adapted to aspirate and dispense liquid into and out of said container;
a Z-axis driving means functionally associated with said backplate and said X-Y head to move the X-Y head in a vertical direction; and
a control system being functionally associated with said shelf driving means to selectively engage the shelf driving means, the control system selectively engaging said Z-axis driving means to move the X-Y head in a vertical direction, the control system selectively controlling the shelf and the X-Y head to cooperatively move to perform said protocol.

21. The pipetting station of claim 20 in which the back plate further comprises at least one horizontal slot, the shelf being functionally associated with the horizontal slot, the shelf being movably attached to the back plate in a cantilever fashion.

22. The pipetting station of claim 21 in which the back plate further comprises a vertical slot, the X-Y head being movably associated with the vertical slot in the back plate.

* * * * *

UNITED STATES PATENT AND TRADEMARK OFFICE
CERTIFICATE OF CORRECTION

PATENT NO.      : 6,325,114 B1                                              Page 1 of 1
DATED           : December 4, 2001
INVENTOR(S)     : JoeBen Bevirt, Gabriel Noah Brinton and Eric Rollins It is certified that error appears in the above-identified patent and that said Letters Patent is hereby corrected as shown below:

Column 15,
Line 5, delete "alone" and insert -- along --

Signed and Sealed this

Fourteenth Day of May, 2002

*Attest:*

*Attesting Officer*

JAMES E. ROGAN
*Director of the United States Patent and Trademark Office*